(12) United States Patent
Van Der Zaag et al.

(10) Patent No.: US 11,160,541 B2
(45) Date of Patent: Nov. 2, 2021

(54) BIOPSY CONTAINER

(71) Applicant: KONINKLIJKE PHILIPS N.V., Eindhoven (NL)

(72) Inventors: Pieter Jan Van Der Zaag, Waalre (NL); Bernardus Hendrikus Wilhelmus Hendriks, Eindhoven (NL); Christian Varekamp, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 302 days.

(21) Appl. No.: 16/300,327

(22) PCT Filed: May 9, 2017

(86) PCT No.: PCT/EP2017/061098
§ 371 (c)(1),
(2) Date: Nov. 9, 2018

(87) PCT Pub. No.: WO2017/194563
PCT Pub. Date: Nov. 16, 2017

(65) Prior Publication Data
US 2019/0105024 A1 Apr. 11, 2019

(30) Foreign Application Priority Data
May 10, 2016 (EP) .................................. 16169008

(51) Int. Cl.
*A61B 10/02* (2006.01)
*A61B 10/00* (2006.01)
(Continued)

(52) U.S. Cl.
CPC ...... *A61B 10/0275* (2013.01); *A61B 10/0096* (2013.01); *A61B 90/39* (2016.02);
(Continued)

(58) Field of Classification Search
CPC . A61B 10/0275; A61B 10/0096; A61B 90/39; A61B 2010/045; A61B 2090/3937
See application file for complete search history.

(56) References Cited

U.S. PATENT DOCUMENTS 5,158,084 A 10/1992 Ghiatas
5,161,542 A * 11/1992 Palestrant .......... A61B 10/0275
600/567
(Continued)

FOREIGN PATENT DOCUMENTS

CN 105101883 A * 11/2015 ......... A61B 10/0096
CN 105517496 A * 4/2016 ......... A61B 10/0266
(Continued)

OTHER PUBLICATIONS

Translation of Speeg, Trevor W V, CN-105101883-A, Nov. 25, 2015 (Year: 2015).*
(Continued)

*Primary Examiner* — Jill A Warden
*Assistant Examiner* — Henry H Nguyen
(74) *Attorney, Agent, or Firm* — Sherry Austin

(57) ABSTRACT

The invention relates to a biopsy container, a biopsy device, an imaging system, and a method for processing images of a biopsy container. The biopsy container comprises a container orientation mark and an alignment mark. The container orientation mark is configured for a cooperation with a corresponding shaft orientation mark arranged on a tube shaft of a biopsy device to indicate a specific orientation of the biopsy container relative to the tube shaft. The alignment mark is configured for a registration of images of the biopsy container.

19 Claims, 5 Drawing Sheets

(51) Int. Cl.
*A61B 90/00* (2016.01)
*A61B 10/04* (2006.01)

(52) U.S. Cl.
CPC ......... *A61B 10/02* (2013.01); *A61B 2010/045* (2013.01); *A61B 2090/3937* (2016.02)

(56) References Cited

U.S. PATENT DOCUMENTS

| | | | |
|---|---|---|---|
| 5,692,519 | A | 12/1997 | Luderer |
| 6,097,994 | A | 8/2000 | Navab |
| 6,099,541 | A | 8/2000 | Klopotek |
| 6,432,064 | B1 | 8/2002 | Hibner |
| 7,465,279 | B2 * | 12/2008 | Beckman ............... A61B 90/39 600/566 |
| 8,128,577 | B2 | 3/2012 | Viola |
| 8,529,465 | B2 | 9/2013 | Speeg |
| 9,107,651 | B2 | 8/2015 | Satoh |
| 9,788,819 | B2 | 10/2017 | Householder |
| 10,463,349 | B2 * | 11/2019 | Van Der Zaag ..... A61B 5/0073 |
| 2011/0125054 | A1 | 5/2011 | Clements |
| 2013/0188855 | A1 | 7/2013 | Desjardins |
| 2014/0127746 | A1 * | 5/2014 | Kachur .................... G01N 1/36 435/40.52 |
| 2014/0193848 | A1 * | 7/2014 | Kaufman ................ B01L 3/508 435/29 |
| 2015/0045665 | A1 | 2/2015 | Lau |
| 2015/0083893 | A1 * | 3/2015 | Wismueller ....... G01N 33/4833 250/208.1 |
| 2016/0192860 | A1 | 7/2016 | Allenby |
| 2017/0319186 | A1 | 11/2017 | Van Der Zaag |

FOREIGN PATENT DOCUMENTS

| | | |
|---|---|---|
| EP | 2016907 A2 | 1/2009 |
| JP | H09193995 A | 7/1997 |
| JP | 2004226228 A | 8/2004 |
| RU | 2135090 C1 | 8/1999 |
| WO | 2007021904 A2 | 2/2007 |
| WO | 2010063293 A1 | 6/2010 |
| WO | 2013105095 A1 | 7/2013 |
| WO | WO-2014042890 A1 * | 3/2014 ........... G01N 29/226 |
| WO | 2014068468 A1 | 5/2014 |
| WO | WO-2015158577 A1 * | 10/2015 ............. A61B 34/20 |
| WO | 2017109201 A1 | 6/2017 |
| WO | 2018041745 A1 | 3/2018 |

OTHER PUBLICATIONS

Translation of Keller, B R , CN-105517496-A, Apr. 20, 2016 (Year: 2016).*
Verhaegh, Wim et al., "Selection of personalized patient therapy through the use of knowledge-based computational models that identify tumor-driving signal transduction pathways" Cancer Res 74 (2014) 2936-45.
Chung, Kwanghun et al Structural and molecular interrogation of intact biological system, Nature, 497 (2013).
Krucker, Jochen et al "Electromagnetic Tracking for Thermal Ablation and Biopsy Guidance: Clinical Evaluation of Spatial Accuracy" J. Vasc. Interv. Radiol. 18 (2007) pp. 1141-1150.
Kadoury, Samuel et al "Real time TRUS/MRI fusion targeted-biopsy for prostate cancer: A clinical demonstration of increased positive biopsy rates", Proc. 13th Int'l Conf. Medical Image Computing and Computer-Assisted Intervention (MICCAI), Beijing, China, Sep. 2010, 52-62.
PCT International Search Report, International application No. PCT/EP2017/061098, dated Sep. 13, 2017.
Observations on the PCT International Search Report and the Written Opinion of International Application No. PCT/EP2017/061098, dated Jun. 13, 2018.

* cited by examiner

BIOPSY CONTAINER

CROSS-REFERENCE TO RELATED APPLICATIONS

This patent application claims the priority benefit under 35 U.S.C. § 371 of international patent application no. PCT/EP2017/061098, filed May 9, 2017, which claims the priority benefit European patent Application No. 16169008.6, filed on May 10, 2016, the contents of which are herein incorporated by reference.

FIELD OF THE INVENTION

The invention relates to a biopsy container, a biopsy device, an imaging system, and a method for processing images of a biopsy container.

BACKGROUND OF THE INVENTION

WO 2014/068468 A1 discloses a biopsy device comprising a tubular member, a hollow shaft and an elongated fiber body. The hollow shaft may have a distal end and a shaft, wherein a laterally facing notch is formed in the distal portion of the shaft. The elongated fiber body may include at least one optical fiber with a distal end. The fiber body is movable within the shaft. The tubular member is movable relative to the shaft, between a first position in which the notch is covered by the tubular member, and a second position in which the notch is not covered by the tubular member.

For the proper analysis of tumors and for defining the appropriate treatment, detailed information on the tumor is needed. First, the presence and position of a potential tumor needs to be identified through medical imaging. Subsequently, a biopsy needs to be taken to assess whether or not the lesion is benign or malignant through pathology. Further, molecular diagnostic (MDx) analysis of the tissue needs to be done to determine which molecular mutations and molecular pathway(s) drive the tumor growth in order to arrive at a proper treatment.

Proper analysis of tumors is increasingly relevant for neo-adjuvant treatment (where drugs are given to shrink the tumor prior to surgery, especially in case of a large tumor) and, in case of treatment with targeted drugs, to determine which target signal transduction pathways are driving tumor growth. Hence, the biopsy does not form just an assessment whether a person has cancer, but is also used for a possibly complete diagnosis including MDx/pathway analysis.

A biopsy device can still be improved to allow an increased gain of information from a tissue sample or biopsy.

SUMMARY OF THE INVENTION

Hence, there may be a need to provide an improved biopsy container, which allows increased gain of information from a biopsy.

The problem of the present invention is solved by the subject-matters of the independent claims, wherein further embodiments are incorporated in the dependent claims. It should be noted that the aspects of the invention described in the following apply also to the biopsy container, the biopsy device, the imaging system, and the method for processing images of a biopsy container.

According to the present invention, a biopsy container is presented. The biopsy container comprises a container orientation mark and an alignment mark. The container orientation mark is configured for a cooperation with a corresponding shaft orientation mark arranged on a tube shaft of a biopsy device to indicate a specific orientation of the biopsy container relative to the tube shaft. The alignment mark is configured for a registration of images of the biopsy container.

A gain of information from a biopsy is improved by using such biopsy container, because this biopsy container allows a registration of image data of the biopsy container with e.g. other image data. The registration of different image data allows an improved and deeper evaluation of both image data.

This biopsy container and in particular the registration of images of the biopsy container may allow that image data of the biopsy are correlated to image data of a patient. The image data of the biopsy may be a 3D analysis of the biopsy. The image data of the patient may be medical image data of e.g. a part of a tumor. The functional form or equation describing the form of the alignment mark may be used for image processing. As a result, it may be possible to register an optical image data obtained from the biopsy, for instance on cancer growth pattern, back to the medical image of the biopsy container and therefore of the tumor from which the biopsy was taken and therefore also to a position of the cancer growth pattern on the patient. In other words, it may be possible to relate biopsy or tissue architecture to medical image data to provide integrated oncology solutions. By this combination of image data of the biopsy and image data of the patient, the gain of information from biopsy is increased.

Further, the biopsy container and in particular the registration of images of the biopsy container may serve to correlate image data obtained from the biopsy to other medical image data that may be available on the tumor. It may be possible to link a 3D location of the biopsy to a location on other imaging modalities, which is important for a combined analysis of pathology and MDx data with other imaging modalities as e.g. MRI, X-ray, ultrasound, etc. Spatial registration of different sources of information improves the gain of information from biopsy and is important for integrated oncology solutions.

Furthermore, the registration of images of the biopsy container may serve to correlate image data obtained from the biopsy to optical image data of the biopsy container taken under different angles of the biopsy tube. As a result, the alignment mark may allow a spatial registration of images taken from multiple angles. Thereby, 3D analysis and visualization and the gain of information from the biopsy is improved.

The biopsy container is configured to receive tissue to be taken as biopsy. The biopsy container may allow directly embedding the biopsy (sample) in the container which makes it easier to remove the biopsy from the biopsy taking shaft or needle and has the advantage of keeping the biopsy intact. The biopsy container may have any kind of shape and cross section. Exemplarily, the biopsy container has a round or an angled cross section. Exemplarily, the biopsy container is a biopsy tube.

This biopsy container and in particular the container orientation mark indicates a specific rotational orientation of the biopsy container relative to the tube shaft, such that the biopsy container can only be inserted into the biopsy device in a single, predefined way. In an example, the container orientation mark is a visual mark. In an example, the container orientation mark is a mechanic mark. In an example, one of the container orientation mark and the shaft orientation mark comprises a protrusion (as e.g. an edge)

and the other an indention (as e.g. a groove) matching the protrusion. The protrusion or indention forming the mechanic container orientation mark may visually indicate a specific rotational orientation of the biopsy container relative to the tube shaft.

The container orientation mark is not essential for the present invention. The container orientation mark and the alignment mark may be different marks, which means there are at least two marks. The container orientation mark and the alignment mark may also be the same mark, which means there is only one mark. In other words, the container orientation mark can also be formed by the alignment mark, while the shaft orientation mark can also be formed by a shaft marker discussed further below.

The alignment mark may have a given functional form, which means the alignment mark may be small and/or thin enough not to occlude important features in the images, may be straightforward to recognize and/or extract in an image stack, and/or may allow unambiguous determination of 3D orientation and translation of a microscopic z-stack with high precision. A z-stack comprises image data taken at multiple positions by means of a 3D microscope which captures for example oblique sections of a sample at each scan step to obtain a 3D image. By means of the alignment mark, these image data can be automatically spatially registered into a single coordinate system. This applies also for the case of creating two z-stack scans, each corresponding to a different orientation of the biopsy container and then registering both z-stack scans in a common coordinate system based on an analysis of where the alignment mark is detected in both z-stacks.

Above requirements for the functional form of the alignment mark may lead to an alignment mark comprising an e.g. opaque, thin, straight line along the biopsy container. Such line does not occlude a single large structure, is straightforward to recognize and/or extract in an image stack, and is good for high precision estimation of 3D orientation and translation. As a 3D volume can be rotated around this straight line in 3D space, the alignment mark may further comprise a second line placed along the biopsy container. Further, a circular dot may be placed at a start of each line. The dots fix an origin of an own unique coordinate system of the biopsy container while the specific placement (90° rotation around the biopsy container) fixes a handedness of this coordinate system. As a result, flexibility in placing the biopsy container at any orientation and in scanning the biopsy container from all directions is achieved.

This structure of the alignment mark may remove all ambiguities as a respective cross section of the biopsy container with these two lines and their dark start dots shows a coordinate system that uniquely determines the 3D geometry of the biopsy container. Each image in a focal z-stack may then have only part of a line sharp. After or prior to image scanning, one can start the calibration procedure by first finding the image that images the start dots as sharp as possible. Using this image as starting point, it can be looped through the images and followed each line through the images by searching pixels values that are dark (light absorbing) and sharp. In each image, it can be searched locally for the pixel that is sharpest and satisfies the darkness assumption. After segmenting the two lines, line equations in the image acquisition coordinate system can be determined after which image analysis results can be mapped into a coordinate system of the biopsy container.

In an example, the alignment mark comprises a line. In an example, the line is continuous, as e.g. a straight line. Exemplarily, the line is interrupted, as e.g. a dotted or dashed line or combinations thereof.

In an example, the alignment mark comprises a curve. Exemplarily, the curve is continuous, as e.g. a spiral. Exemplarily, the curve is interrupted, as e.g. a dotted or dashed spiral or combinations thereof.

In an example, the alignment mark comprises two lines or curves. The number of two may help to reduce orientation ambiguities as a respective cross section of the biopsy container with these two lines or curves shows a coordinate system that determines the orientation 3D geometry of the biopsy container. In an example, the two lines or curves are arranged parallel to each other. In another example, the two lines or curves are arranged at different parts of the biopsy container. Exemplarily, the two lines or curves are arranged at different ends of the biopsy container. Exemplarily, the alignment mark comprises three lines or curves. Exemplarily, the alignment mark comprises a combination at least a line and a curve.

In an example, a starting point of the alignment mark is provided with a starting symbol. Exemplarily, the starting symbol is a starting dot, a filled circle, has a diamond shape or the like. The starting point may help to remove any remaining ambiguity and also help the design of a detection algorithm.

The alignment mark, e.g. in form of lines or curves, may run essentially along a length of the biopsy container. The alignment mark may also extend along the entire length of the biopsy container. Having an essentially longitudinal alignment mark with known geometry enables a detection of the alignment mark as well as a calibration of the images and thereby allows moving a scanning camera sensor as well as rotating the biopsy container in order to image the biopsy container from all sides. Further, such essentially longitudinal alignment has the advantage that multiple z-stacks taken at multiple positions and/or with multiple orientations can be automatically spatially registered into a single common coordinate system.

The alignment mark may also have only a small extension and be e.g. a dot, a cross, an X, an asterisk, a letter, several letters, a number, several numbers and/or the like.

In an example, the alignment mark is detectable by an imaging unit. The imaging unit may be an optical imaging unit. This allows detecting the alignment mark also by the (optical) imaging unit. The alignment mark could therefore be made of an ink comprising magnetic particles. In this way, the alignment mark may be both visible in e.g. an optical pathology microscopic scanner and also, via the magnetic particles, detectable via e.g. MRI imaging. As will be explained further below, the imaging unit may also detect a shaft marker provided on the tube shaft.

In an example, the alignment mark is provided on a surface of the biopsy container. In another example, the alignment mark is embedded or incorporated into a surface of the biopsy container. The biopsy container may be made of glass and the alignment mark may be cut into the glass.

In another important example, the biopsy container only comprises the alignment mark configured for a registration of images of the biopsy container. There is no container orientation mark. There is no function of a cooperation with a corresponding shaft orientation mark arranged on a tube shaft of a biopsy device to indicate a specific orientation of the biopsy container relative to the tube shaft.

The alignment mark allows a registration of image data of the biopsy container with e.g. other image data. The registration of different image data allows an improved and deeper evaluation of both image data.

All said above in view of the alignment mark combined with the container orientation mark also applies without the container orientation mark. In particular, the alignment mark may comprise a given functional form as e.g. at least a line, at least a curve, at least a starting point, etc. It can run essentially along an entire length of the biopsy container. The alignment mark may also have only a small extension and be e.g. a dot, a cross and/or the like. It may be visually detectable by e.g. an imaging unit. The alignment mark may be provided on or embedded into a surface of the biopsy container.

The alignment mark may work as container orientation mark. Then, the alignment mark may be configured for a cooperation with a shaft orientation mark of the tube shaft to indicate a specific orientation of the biopsy container relative to the tube shaft. In other words, the container orientation mark is formed by the alignment mark, while the shaft orientation mark is formed by a shaft marker discussed further below.

According to the present invention, also a biopsy device is presented. The biopsy device comprises a biopsy container as described above and a tube shaft. A container orientation mark of the biopsy container is configured for a cooperation with a corresponding shaft orientation mark of the tube shaft to indicate a specific orientation of the biopsy container relative to the tube shaft.

In an example, one of the container orientation mark and the shaft orientation mark comprises a protrusion and the other an indention matching to the protrusion.

The biopsy device allows tracing results of an analysis of a biopsy back to image data of the original tissue, e.g. a tumor, which has been biopsied. The biopsy container therefore comprises an alignment mark. In an example, the alignment mark has a given functional form as e.g. at least one line or curve.

In an example, the tube shaft is provided with a shaft marker configured for an alignment with the alignment mark of the biopsy container. The shaft marker can be used in the aforementioned registration process, but can also let a pathologist know how to mount, align and fix the biopsy container in the tube shaft. Further, the shaft marker can be used to let the pathologist know how the biopsy container is positioned within the tube shaft, which is suitable for referencing back to image data of the patient. In other words, the shaft marker can be used to help the pathologist to align and know an orientation of the tube shaft and the biopsy container with respect to each other.

The shaft marker may be one of a dot, a cross, a line or the like corresponding to one of a dot, a cross, a line or the like on the biopsy container, which the person inserting the biopsy container would have to align to another so that they lie next to each other. For instance, a cross and a line can be used as long as one part of the cross can be lined-up in the extension of the line. This way, a user can see that the alignment of the biopsy tube in the biopsy needle is correct.

In an example, the shaft marker is detectable by an imaging unit. This imaging unit may be the first imaging unit, which means the one described above for detecting the alignment mark, or a different, second imaging unit. The imaging units may be medical imaging units, as e.g. an MRI, CT, or X-ray system. In an example, the shaft marker is visually and/or optically detectable by e.g. the pathologist and/or an instrument.

Exemplarily, the biopsy tube and the tube shaft are together moveably accommodated in a hollow main shaft. Exemplarily, the biopsy tube is insertable into the tube shaft. Exemplarily, a proximal end of the biopsy tube is releasably attachable to a distal end of the tube shaft.

According to the present invention, also an imaging system is presented. The imaging system comprises an imaging unit, a processing unit, and a biopsy container as described above. The imaging unit is configured to provide images of the biopsy container. The processing unit is configured to register the images of the biopsy container. The processing unit processes the information how the various images of the biopsy container register with each other based on the alignment mark visible in these images to a 3D reconstruction of the biopsy. This information is combined with the information how the biopsy was orientated in the biopsy container based on e.g. a medical image assisted biopsy taking. This combination of information allows knowing how the tissue or the 3D reconstruction of the biopsy was orientated in the patient's body.

According to the present invention, also an imaging method is presented. It comprises the following steps, not necessarily in this order:
a) providing images of a biopsy container as described above,
b) detecting an alignment mark of the biopsy container in the images,
c) determining an orientation of the biopsy container in the images, and
d) performing a registration of the images by means of the alignment mark.

In an example, the registration is performed to a single common coordinate system with a known relation to a coordinate system of a tube shaft.

It shall be understood that the biopsy container, the biopsy device, the imaging system, and the method for processing images of a biopsy container according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
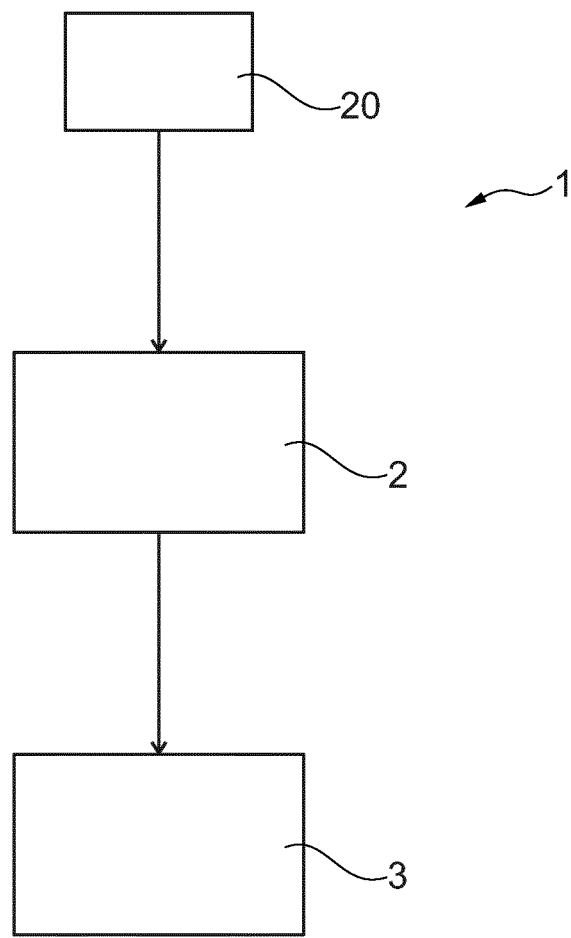
FIG. 1 shows schematically and exemplarily an embodiment of an imaging system according to the invention.

FIG. 1 shows schematically and exemplarily an embodiment of an imaging system 1 according to the invention. The imaging system 1 comprises an imaging unit 2, a processing unit 3, and a biopsy container 20. The biopsy container 20 comprises an alignment mark. The imaging unit 2 is configured to provide images of the biopsy container 20. The imaging unit 2 is here an optical imaging unit, as e.g. an optical transmission or confocal microscope or a two photon imaging device. The processing unit 3 is configured to register the images of the biopsy container 20. The processing unit 3 processes the information how the various images of the biopsy container 20 register with each other based on the alignment mark visible in these images to a 3D reconstruction of the biopsy. This information is combined with the information how the biopsy was orientated in the biopsy container 20 based on e.g. a medical image assisted biopsy taking. This combination of information allows knowing how the tissue or the 3D reconstruction of the biopsy was orientated in the patient's body.

The biopsy container 20 and the registration of the images of the biopsy container 20 are further explained in the following.

The imaging system 1 may be a digital pathology system comprising an optical scanner as imaging unit 2 and an image management system as processing unit 3 to enable digitizing, storage, retrieval, and processing of tissue images, preferably tissue staining images, reading the information stored in the storage box container, and integrating this information with the digitized staining data set, to be presented to the pathologist.

Figure 2:
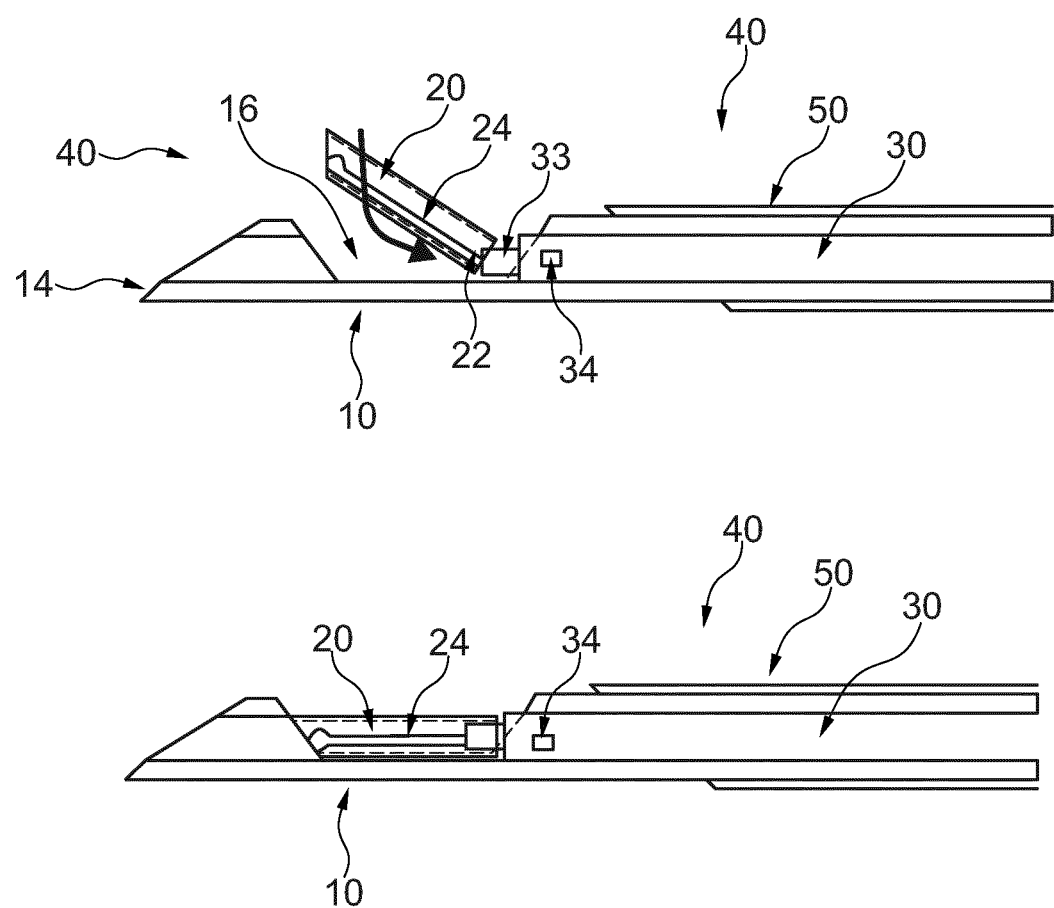
FIG. 2 shows schematically and exemplarily an embodiment of the biopsy device according to the invention.

FIG. 2 shows schematically and exemplarily an embodiment of a biopsy device 40 according to the invention. The biopsy device 40 comprises the biopsy container 20 and a tube shaft 30. The biopsy container 20 is configured to receive tissue to be taken as biopsy. The biopsy container 20 is here a biopsy tube which is substantially formed as a hollow cylinder with a substantially circular outer cross section. The biopsy container 20 comprises here an alignment mark 24 in form of two straight lines extending essentially along the entire length of the biopsy container 20 with a marked starting point. The alignment mark 24 will be explained in detail to FIGS. 4 and 5.

The biopsy device 40 comprises an outer sleeve 50, in which a hollow main shaft 10 with a distal end or tip 14 forming an optionally slanted surface is accommodated, wherein the slanted surface may have an oval shape in case the hollow shaft 10 has a circular cross section.

The structure of the biopsy device 40 described in the following is only an option. A lateral recess or notch 16 is formed in the tube shaft 30, wherein the notch 16 is substantially formed by a lateral opening and a section of the bore extending through the tube shaft 30 in a longitudinal direction. FIG. 2 further illustrates as to how a biopsy container 20 may be inserted into the notch 16 of the hollow shaft 10 of the biopsy device 40 so as to be attached at a distal end 33 of the tube shaft 30.

For example, the biopsy container 20 may be inserted with an inclined orientation and with a proximal end 22 first. This may have the advantage that an attachment of the biopsy container 20 to the distal end 33 of the tube shaft 30 may be better controlled by hand. The kind of movement of this example is indicated by the bold arrow in FIG. 2.

Alternatively, the biopsy container 20 may be inserted into the notch 16 of the main shaft 10 with a parallel orientation of the longitudinal axis of the biopsy container 20 and the longitudinal axis of the hollow main shaft 10. In this case, the tube shaft 30 may be pulled a few millimetres backwards, i.e. proximally, to provide sufficient space for the biopsy container 20 to be inserted into the notch 16.

Subsequently, the tube shaft 30 may be pushed forwards, i.e. distally, so that the distal end 33 with the reduced diameter may engage the biopsy container 20 so as to attach the biopsy container 20 to the tube shaft 30.

The shown biopsy container 20 allows directly embedding the biopsy in the biopsy container 20 which makes it easier to remove the biopsy from the tube shaft 30 and has the advantage of keeping the biopsy intact.

Figure 3:
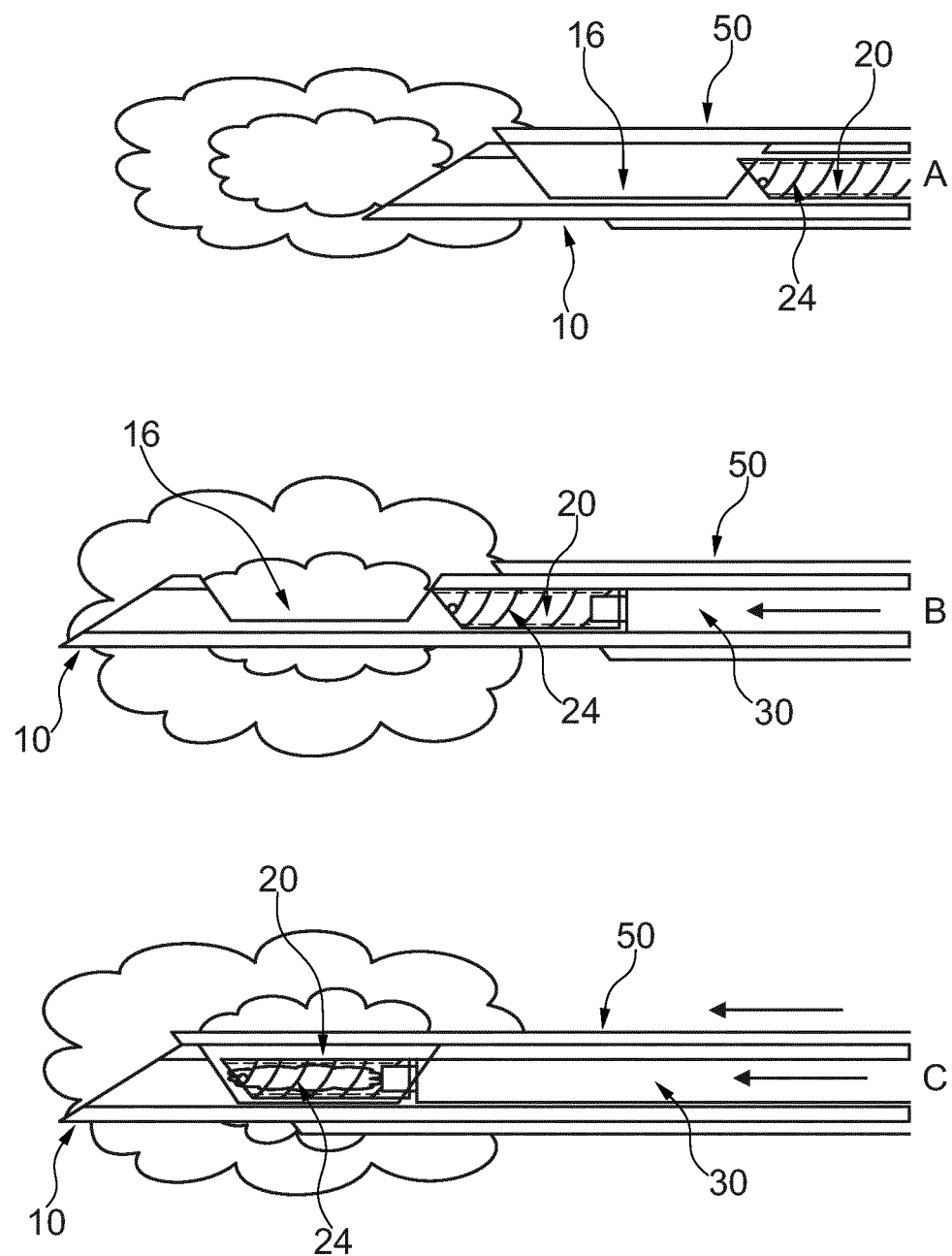
FIG. 3 shows a sequence of steps of taking a biopsy by means of the biopsy device according to the invention.

FIG. 3 shows a sequence of steps of taking a biopsy by means of the biopsy device 40 including, inter alia, the biopsy container 20 for receiving tissue. Firstly, with the notch 16 of the hollow shaft 10 being covered by the outer sleeve 50, the biopsy device 40 is inserted into tissue. Secondly, the hollow shaft 10 is pushed forward until the notch 16 in the hollow main shaft 10 is no longer covered so that tissue can engage the notch 16. Thirdly, the outer sleeve 50 which is provided with a sharp distal edge is pushed forwards so as to cut the tissue and the tube shaft 30 with the biopsy container 20 is pushed forward so as to receive the cut tissue. It is noted that the outer sleeve 50 may also have a blunt distal edge, i.e. not a sharp distal edge, and that the biopsy container 20 may be provided with a sharp distal edge, so that tissue which is present in the notch 16 of the hollow shaft 10 can be cut by means of the biopsy container 20.

In this example, the alignment mark 24 is shown in form of a spiral extending essentially along the entire length of the biopsy container 20 with a marked starting point. The alignment mark 24 will be explained in detail to FIGS. 4 and 5.

Figure 4:
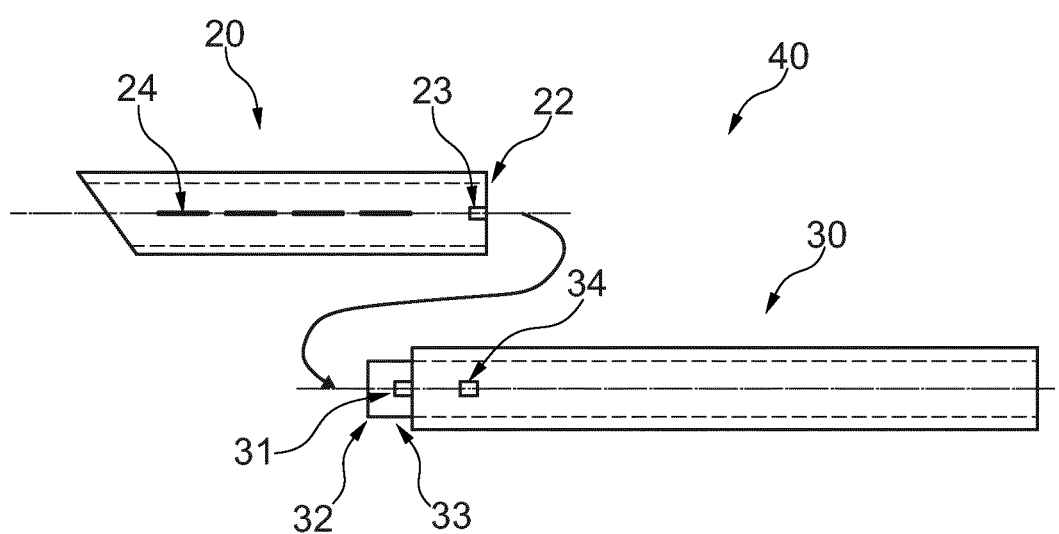
FIG. 4 shows schematically and exemplarily an embodiment of the biopsy device according to the invention.

FIG. 4 shows schematically and exemplarily an embodiment of the biopsy device 40 according to the invention. The biopsy device 40 comprises the biopsy container 20 and the tube shaft 30. The biopsy container 20 comprises a container orientation mark 23 and an alignment mark 24. The container orientation mark 23 is configured for a cooperation with a corresponding shaft orientation mark 31 arranged on the tube shaft 30 to indicate a specific orientation of the biopsy container 20 relative to the tube shaft 30, such that the biopsy container 20 can only be inserted into the biopsy device 40 in a single, predefined way. As container orientation mark 23, the biopsy container 20 is here provided with an indention or groove at a first end 22 of the biopsy container 20. The groove is configured for a cooperation with a protrusion or edge as shaft orientation mark 31, which is formed at a first end 32 of the tube shaft 30. The container orientation mark 23 and the shaft orientation mark 31 are useful in identifying a rotational orientation of a biopsy sample during later handling and analysis. Here, the groove at the end of the biopsy container 20 forms the container orientation mark 23. It notably enables visually indicating a specific rotational orientation of the biopsy container 20 relative to the tube shaft 30.

The alignment mark 24 of the biopsy container 20 is configured for a registration of images of the biopsy container 20. The alignment mark 24 is detectable by an imaging unit 2 and is provided on a surface of the biopsy container 20. The alignment mark 24 is here a single dashed line extending essentially along the length, preferably the entire length of the biopsy container 20.

The registration of images of the biopsy container 20 allows that image data of the biopsy are correlated to image data of a patient. This may be done as follows:

By means of the alignment mark 24, the various images may be aligned to each other to form a 3D image of the biopsy.

As the alignment of the biopsy container 20 in the tube shaft 30 or biopsy needle is known, also the position of the biopsy container 20 with respect to the tube shaft 30 is known.

From image guided biopsy taking, the position of the tube shaft 30 with respect to the patient is known.

The fact that the alignment mark 24 may be detected by the medical imaging modalities gives an additional handle on its position in the patient.

As a result, it is possible to register an optical image data obtained from the biopsy, for instance on cancer growth pattern, back to the medical image of the biopsy container 20 and therefore of the tumour from which the biopsy was taken and therefore also to a position of the cancer growth pattern on the patient. In other words, it is possible to relate biopsy architecture to medical image data to provide integrated oncology solutions.

Further, the registration of images of the biopsy container 20 serves to correlate image data obtained from the biopsy to other medical image data that may be available on the tumour. It may be possible to link a 3D location of a biopsy to a location on other imaging modalities, which is important for a combined analysis of pathology and MDx data with other imaging modalities as e.g. X-ray, ultrasound, etc.

The registration of images of the biopsy container 20 further serves to correlate image data obtained from the biopsy to optical image data of the biopsy container 20 taken under different angles of the biopsy container 20. As a result, the alignment mark 24 may allow a spatial registration of images taken from multiple angles. Thereby, 3D analysis and visualization is improved.

Figure 5:
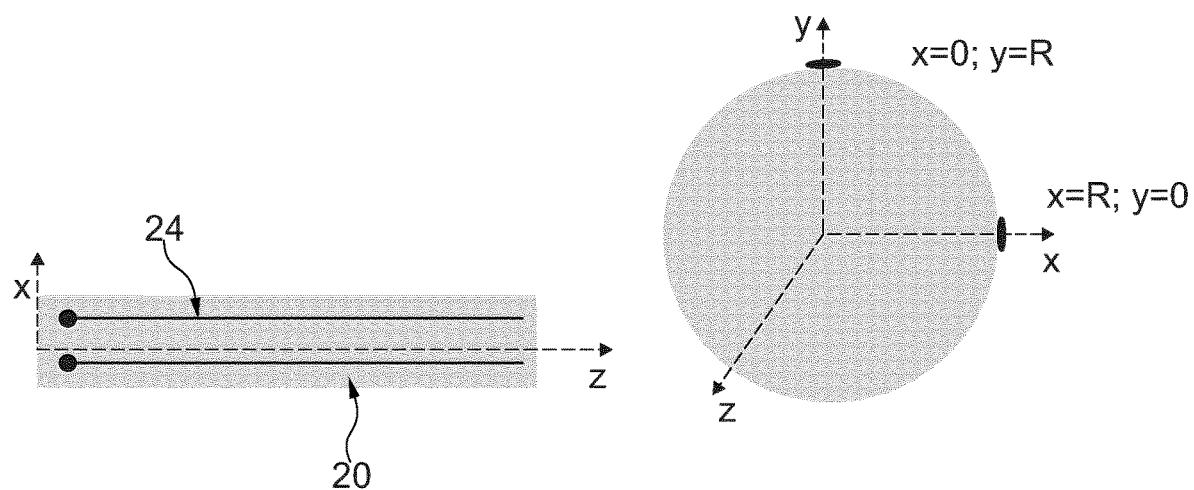
FIG. 5 shows schematically and exemplarily an embodiment of the biopsy container with the alignment mark according to the invention.

FIG. 5 shows schematically and exemplarily an embodiment of the biopsy container 20 with the alignment mark 24 according to an embodiment of the invention. On the left side, the biopsy container 20 is shown, while on the right side, an enlarged cross section of the biopsy container 20 is shown. The alignment mark 24 comprises here two opaque, thin, continuous, straight lines arranged parallel to each other along the biopsy container 20. Further, a circular dot is placed at a start of each line. The dots fix an origin of an own unique coordinate system of the biopsy container 20 while the specific placement (90° rotation around the biopsy container 20) fixes a handedness of this coordinate system. As a result, the registration can be performed to a single common coordinate system of the biopsy container 20 with a known relation to a coordinate system of the tube shaft 30.

This structure of the alignment mark 24 removes all ambiguities as a respective cross section of the biopsy container 20 with these two lines and their dark start dots shows a coordinate system that uniquely determines the 3D geometry of the biopsy container 20. Each image in a focal z-stack may then have only part of a line sharp. The z-stack comprises image data taken at multiple positions by means of a 3D microscope which captures oblique sections of a sample at each scan step to obtain a 3D image. After image scanning, one can start the calibration procedure by first finding the image that images the start dots as sharp as possible. Using this image as starting point, it can be looped through the images and followed each line through the images by searching pixels values that are dark and sharp. In each image, it can be searched locally for the pixel that is sharpest and satisfies the darkness assumption. After segmenting the two lines, line equations in the image acquisition coordinate system can be determined after which image analysis results can be mapped into a coordinate system of the biopsy container 20.

The tube shaft 30 is provided with a shaft marker 34 configured for an alignment with the alignment mark 24 of the biopsy container 20. The shaft marker 34 can be used in the aforementioned registration process, but can also be used to know how the biopsy container 20 is positioned within the tube shaft 30, which is suitable for referencing back to image data of the patient.

Figure 6:
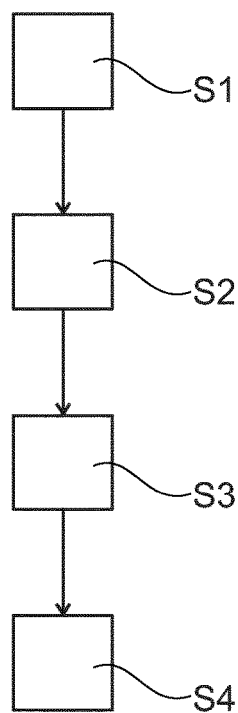
FIG. 6 shows a schematic overview of steps of an imaging method according to the invention.

FIG. 6 shows a schematic overview of steps of an imaging method according to the invention. The imaging method comprises the following steps, not necessarily in this order:

In a first step S1, providing images of a biopsy container 20 as described above.

In a second step S2, detecting an alignment mark 24 of the biopsy container 20 in the images.

In a third step S3, determining an orientation of the biopsy container 20 in the images.

In a fourth step S4, performing a registration of the images by means of the alignment mark 24.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A biopsy container, comprising:
   a hollow cylinder comprising an open proximal end and an open distal end;
   a container orientation mark located adjacent the proximal end and having an indentation or groove; and
   an alignment mark,
   wherein the container orientation mark is configured for cooperation, using the indentation or groove, with a corresponding shaft orientation mark having a protrusion or edge and arranged on a tube shaft of a biopsy device to indicate a specific orientation of the biopsy container relative to the tube shaft, and wherein the alignment mark is configured for a registration of images of the biopsy container.

2. The biopsy container of claim 1, wherein the container orientation mark and the alignment mark are the same mark.

3. The biopsy container of claim 1, wherein the container orientation mark and the alignment mark are different marks.

4. The biopsy container of claim 1, wherein the alignment mark comprises a line.

5. The biopsy container of claim 4, wherein the line is continuous.

6. The biopsy container of claim 1, wherein the alignment mark comprises a curve.

7. The biopsy container of claim 1, wherein the alignment mark comprises two lines or curves.

8. The biopsy container of claim 7, wherein the two lines or curves are arranged parallel to each other.

9. The biopsy container of claim 7, wherein the two lines or curves are arranged at different parts of the biopsy container.

10. The biopsy container of claim 1, wherein a starting point of the alignment mark is provided with a starting symbol.

11. The biopsy container of claim 1, wherein the alignment mark, the container orientation mark and/or the shaft orientation mark are detectable by an imaging unit.

12. The biopsy container of claim 1, wherein the alignment mark is provided on a surface of the biopsy container.

13. The biopsy container of claim 11, wherein the alignment mark is embedded into a surface of the biopsy container.

14. The biopsy container of claim 13, wherein the container orientation mark and the shaft orientation mark are visual marks.

15. The biopsy container of claim 13, wherein one of the container orientation mark and the shaft orientation mark comprises a protrusion and the other an indention matching to the protrusion.

16. A biopsy device, comprising: a biopsy container comprising a container orientation mark and an alignment mark, and a tube shaft, wherein the container orientation mark is configured for a cooperation with a corresponding shaft orientation mark of the tube shaft to indicate a specific orientation of the biopsy container relative to the tube shaft, and wherein the alignment mark is configured for a registration of images of the biopsy container.

17. The biopsy device of claim 16, wherein the tube shaft is provided with a shaft marker configured for an alignment with an alignment mark of the biopsy container.

18. The biopsy device of claim 17, wherein the shaft marker is detectable by an imaging unit.

19. An imaging system, comprising:
an imaging unit,
a processing unit, and
a biopsy container according to claim 1,
wherein the imaging unit is configured to provide images of the biopsy container, and
wherein the processing unit is configured to register the images of the biopsy container.

\* \* \* \* \*